US006384263B1

(12) United States Patent
Herkes

(10) Patent No.: US 6,384,263 B1
(45) Date of Patent: May 7, 2002

(54) PROCESS FOR MAKING 3-HYDROXYALKANELNITRILES AND CONVERSION OF THE 3-HYDROXYALKANELNITRILE TO AN HYDROXYAMINOALKANE

(75) Inventor: Frank E. Herkes, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/916,604

(22) Filed: Jul. 27, 2001

Related U.S. Application Data
(60) Provisional application No. 60/223,038, filed on Aug. 4, 2000.

(51) Int. Cl.[7] .................. C07C 255/00; C07C 209/00
(52) U.S. Cl. ........................................ 558/451; 564/490
(58) Field of Search ........................... 558/451; 564/490

(56) References Cited

U.S. PATENT DOCUMENTS

| 4,355,181 A | 10/1982 | Willis, Jr. et al. |
| 4,567,303 A | 1/1986 | Boettger et al. |
| 4,605,769 A | 8/1986 | Green |
| 4,931,596 A | 6/1990 | Laurenzo |
| 5,599,999 A | 2/1997 | Moriya et al. |
| 5,633,408 A | 5/1997 | Watanabe et al. |

FOREIGN PATENT DOCUMENTS

| FR | 1446127 | 9/1965 |
| JP | 05317066 A | 12/1993 |
| JP | 07033718 A | 2/1995 |

*Primary Examiner*—T. A. Solola
*Assistant Examiner*—Joseph Murray

(57) ABSTRACT

The present invention provides a process for making 3-hydroxyalkanenitriles comprising the steps of reacting an alkenylnitrile, wherein the alkenylnitrile is an alkenyl-2-nitrile or an alkenylnitrile which under reaction conditions isomerizes to form an alkenyl-2-nitrile, in the presence of a base with benzyl alcohol to form a 3-benzyloxyalkanenitrile adduct and then partially hydrogenating the adduct in the presence of a trace amount of HCl to form the 3-hydroxyalkanenitrile or fully hydrogenating the adduct to form a 3-hydroxyaminoalkane.

7 Claims, No Drawings

PROCESS FOR MAKING 3-HYDROXYALKANELNITRILES AND CONVERSION OF THE 3-HYDROXYALKANELNITRILE TO AN HYDROXYAMINOALKANE

The instant application claims priority to Provisional Application No. 60/223,038 filed Aug. 4, 2000.

FIELD OF THE INVENTION

The present invention provides a process for making 3-hydroxyalkanenitriles comprising the steps of reacting certain alkenylnitriles with benzyl alcohol in the presence of a base to form a 3-benzyloxyalkanenitrile adduct and then partially hydrogenating the adduct to form the 3-hydroxyalkanenitrile. The adduct may also be fully hydrogenated to form a 3-hydroxyaminoalkane.

BACKGROUND OF THE INVENTION

The synthesis of hydroxyalkanenitriles from reactions of epoxides with HCN is known. For example in French patent 1446127 teaches the preparation of cyanohydrins by treating epoxides with HCN in the presence of an alkyl aluminum compound. 3-hydroxyalkanenitriles have also been prepared from 1,2-epoxides using halohydrin epoxidase of corynebacterium in JP-05317066.

Alkanolamines(which are also referred to herein as hydroxyaminoalkanes) have been prepared by reaction of alkylene oxides with ammonia in the presence of a variety of catalysts. For example, U.S. Pat. No. 5,633,408 teaches reacting the alkylene oxide with ammonia in the presence of ammonium carbonate; U.S. Pat. No. 5,599,999 teaches the reaction of alkylene oxide with ammonia in the liquid phase over a rare earth catalyst. Other methods for making alkanolamines starting from alkylene oxides include U.S. Pat. Nos. 4,567,303; 4,355,181; 4,605,769; 4,931,596; and JP-07033718A.

The present inventor wished to use a simple addition reaction using pentenenitriles as the starting material for the synthesis of the 3-hydroxyalkanenitriles. After much experimental work he found that routes used to add water to molecules such as acrolein and acrylonitrile did not provide a workable method for the synthesis of 3-hydroxyalkanenitriles starting from pentenenitriles. The object of the present invention is to provide routes to 3-hydroxyalkanenitriles and alkanolamines using a Michael-type addition reaction followed by hydrogenation.

SUMMARY OF THE INVENTION

The present invention provides a process for making 3-hydroxyalkanenitriles comprising the steps of reacting an alkenylnitrile, wherein the alkenylnitrile is an alkenyl-2-nitrile or an alkenylnitrile which under reaction conditions isomerizes to form an alkenyl-2-nitrile, in the presence of a base with benzyl alcohol to form a 3-benzyloxyalkanenitrile adduct and then partially hydrogenating the adduct in the presence of a trace amount of HCl to form 3-hydroxyalkanenitrile.

The present process may be run as a batch, semi-batch or a continuous process.

Acceptable bases for the present process include bases selected from the group consisting of alkali metal hydroxides, alkaline earth metal hydroxides, alkali metal carbonates, alkaline earth metal carbonates, tertiary amines, Lewis bases and strongly basic ion exchange resins.

The 3-hydroxyalkanenitrile product of the present invention may be converted into a hydroxyaminoalkane if, after the formation of the benzyloxyalkanenitrile adduct, the adduct is completely hydrogenated to form a 3-hydroxyaminoalkane.

DETAILED DESCRIPTION

The present invention provides a process for making 3-hydroxyalkanenitriles comprising the steps of reacting certain alkenylnitriles with benzyl alcohol in the presence of a base to form a 3-benzyloxyalkanenitrile adduct and then partially hydrogenating the adduct to form the 3-hydroxyalkanenitrile. The adduct may also be fully hydrogenated to form a 3-hydroxyaminoalkane.

The alkenylnitriles that react according to the present invention are those alkenylnitriles that are $\alpha$, $\beta$ unsaturated. That is the double bond is in the 2 position relative to the CN group.

Particularly useful in the present invention are the 2-pentenenitriles. 2-Pentenenitrile, including the geometric isomers, react directly to form the adduct. The 3- and 4-pentenenitriles isomerize to 2-pentenenitrile under the reaction conditions of the present process to react to form the adduct. These pentenenitriles are by products in the manufacture of adiponitrile and are therefore cost effective starting materials. In the present process, these pentenenitriles may be reacted in mixtures, one with another or all three together, mixed any ratio or may be reacted as isolated compounds.

The benzyl alcohol is generally present in the reaction mixture at about a 2 to 1 molar ratio with the alkenyl-2-nitrile. The base is present in the range of from about 1 to 5% by weight of the reaction mixture.

Many bases are suitable for use in the present process, although ammonia and primary amines must be avoided. Suitable bases include bases selected from the group consisting of alkali metal hydroxides; alkaline earth metal hydroxides, alkali metal carbonates, alkaline earth metal carbonates, tertiary amines, Lewis bases and strongly basic ion exchange resins. It is also possible to use the base in a variety of physical forms. For example, the base may be used as a solution, as an aqueous solution, as solid particles or the base may be supported on solid particles. Solid forms of the base, for example, may be ground or flaked alkali hydroxides such a sodium, potassium or calcium hydroxide or particles of metal carbonates, such as potassium carbonate or calcium carbonate. The base may also be supported on a second particle such as potassium hydroxide deposited on clay, silica, alumina, titania or zirconia. The base may also be used as a (or in) solution either in an inert organic solvent or in water.

Hydroxyalkanenitriles formed in the present process are useful as starting materials for making various polymer classes; raw materials and intermediates for many organosynthesis products, such as pharmaceuticals; agricultural chemicals; a monomer for coatings; and polymer intermediates.

The soft or partial hydrogenation of the adduct to the 3-hydroxyalkanenitrile, is carried out in the presence of a trace amount of HCl over a platinum or palladium catalyst, usually supported. By trace amount of HCl is meant concentrations of HCl in the reaction mixture of from about 0.05 to about 1% by weight HCl.

The hydrogenation of the 3-hydroxyalkanenitrile to form the alkanolamine (or hydroxyaminoalkane) is typically carried out over metal catalysts such as RANEY nickel, RANEY cobalt, RANEY nickel or RANEY cobalt catalysts promoted with chromium, nickel, iron, molybdenum or mixtures of any of these metals (RANEY is a trademark of W. R. Grace and Company). The hydrogenation is typically run at temperatures of from about 75 to about 150° C. and pressures from about 200 to about 4000 psig.

The present process may also be carried out with a solvent present, either alone or in combination with water, in the reaction mixture. Such solvent needs to be inert under the reaction conditions of the process. That is the solvent should not be a material or mixture that will add or otherwise react non-reversibly with the subject pentenenitriles. Preferred solvents include dioxane, tetrahydrofuran, dimethylformamide, dimethylacetamide, methanol, ethanol and isopropanol. Water may be present in the reaction solution. If water is present in the reaction, it is preferred that the water is present at not more than about 5% by weight of the reaction mixture. The most preferred concentration of water is about 2%. In the catalyst mixture used in this full hydrogenation, the catalyst mixture may contain up to 5 weight % aqueous caustic containing from 100 to 1000 ppm of an alkali metal or alkaline earth metal oxide or hydroxide.

The present process may be run a s a batch, semi-batch or a continuous process.

The present process is illustrated by the following examples. These Examples are not intended to limit the invention.

EXAMPLES

Example 1

Cyanobutylation of Benzyl Alcohol with cis-pentenenitrile Catalyzed by Potassium Hydroxide Ground KOH (19.85 g) was added to 300 g benzyl alcohol in a oil jacketed 1 liter round bottomed flask and heated to 45° C. Purified cis 2-pentenenitrile (116.6 g (85% purity, 1.42 moles) was added dropwise from an addition funnel employing a $N_2$ purge such that the temperature was maintained at 500. After the addition, the mixture was heated for an additional two hours. A tea-colored solution was observed at this point.

The product was neutralized at 50° with 32 g 49% sulfuric acid to ~pH 7. After cooling to room temperature, the mixture was vacuum filtered, and the filtrate extracted with 200 mL of methyl-t-butylether. The top organic layer was analyzed by GC on a 30 meter×0.5 mm DB 1701 (J&W) glass capillary column. Analysis of the extract indicated a 96.5% conversion of cis-pentenenitrile and 92.3% selectivity (89.9% yield) to the 1:1 benzyl alcohol-cis-2-pentenenitrile adduct, 3-benzyloxypentanenitrile. A 7.7% selectivity to isomeric pentene nitrites and dimers was also observed.

Example 2

Cyanobutylation of Benzyl Alcohol with cis 2-Pentenenitrile Catalyzed by Potassium Carbonate Potassium carbonate (6.0 g) was suspended in 82 grams of benzyl alcohol in a 500 mL oil-jacketed, round bottom three neck flask. Mixture was moderately stirred using a magnetic stirring bar and heated to 85° C. using an oil bath. Purified cis 2-pentenenitrile (32 g, 98.5% pure) was added dropwise (~0.8 to 1.0 mL/min) from an addition funnel while agitation continued. It should be noted that a condenser was placed between the addition funnel and reaction flask so as to avoid any reactant evaporation. A $N_2$ purge was applied and the temperature maintained at 85° C. Upon complete addition of the cis 2-pentenenitrile to the reaction mixture heating and agitation continued for an additional five hours. After the five hours a clear, amber colored solution was observed.

Using 600 to 700 $\mu$L of 50% (wt/wt%) sulfuric acid, the product was neutralized at the reaction temperature to ~pH 7. After cooling to room temperature the mixture was vacuum filtered and the filtrate analyzed by gc. Analysis of the crude product indicated a 75.4% conversion of cis 2-pentenenitrile and 61.2% selectivity (46.2% yield) to the 1:1 benzyl alcohol-cis-pentenenitrile adduct, 3-benzyloxypentanenitrile.

Example 3

Cyanobutylation of Benzyl Alcohol with cis 2-Pentenenitrile Catalyzed by Potassium Hydroxide Supported on Alumina Into a 300 mL stainless steel autoclave, equipped with a Magnadrive stirrer, cooling coil, thermocouple and sample dip tube, was charged 45 g (0.389 mole) crude cis-2-pentenenitrile (70% cis2-pentenenitrile content), 82.0 g (0.759 mole) benzyl alcohol and 3.0 g KOH/Al2O3 catalyst. The vessel was sealed followed by stirring at 25° for one minute then stopped. The reactor was pressured to 100 psig with nitrogen and heated to 95°. Stirring was started at 1000 rpm and reaction run for three hours. After cooling, the catalyst was filtered and amber product filtrate analyzed by gas chromatography. The conversion of cis-2-pentenenitrile was 82.4% and the yield of 3-benzyloxy-pentanenitrile was 63.5%. Isomerization of cis-2-pentenenitrile to trans-2-pentenenitrile and 3-pentenenitrile were the major by-products.

Example 4

Hydrogenation of 3-Benzyloxypentanenitrile to 3-Hydroxyvaleronitrile

A mixture of 3-benzyloxypentanenitrile (83.3 g, 92% purity), 4.3 wt % benzyl alcohol, 250 mL methanol, 4 g of 36% aqueous HCl and 2.8 g wet 5% Pd/C (Engelhard Escat 111, 1.4 g dry basis) was hydrogenated in a 1000 mL Hastelloy C autoclave at 300 psig and 50° for 1 hour. Analysis of the product, after neutralization with $NaHCO_3$, by GC analysis showed complete conversion of the 2-benzyloxypentanenitrile to 3-hydroxyvaleronitrile and toluene greater than 98% yield. The product (500 g), after removal of methanol, was batch distilled on an Oldershaw column to yield 212 g (99.9% purity) of 3-hydroxyvaleronitrile, bp 116–118°/1.9 mm Hg.

Example 5

Hydrogenation of 3-Hydroxyvaleronitrile to 1-aminopentan-3-ol

A mixture of 50.9 g of 3-hydroxyvaleronitrile, 40 mL tetrahydrofuran and 1.1 g Raney® Co (Raney 2714) was hydrogenated at 800 psig and 90° in a 300 mL stainless steel autoclave equipped with a thermocouple, Magnadrive stirrer and sample dip tube. After three hours, the run was stopped and cooled. The catalyst was filtered and the filtrate analyzed on a 30 meter×0.5 mm ID DB1701 capillary column. GC analysis indicated >99.9% 3-hydroxyvaleronitrile conversion with a 75% yield to 1-aminopentan-3-ol.

What is claimed is:

1. A process for making 3-hydroxyalkanenitrile comprising the steps of reacting an alkenylnitrile, wherein the alkenylnitrile is a 2-alkenylnitrile or a alkenylnitrile which under reaction conditions isomerizes to form a 2-alkenylnitrile, in the presence of a base with benzyl alcohol to form a 3-benzyloxyalkanenitrile adduct and then partially hydrogenating the adduct in the presence of a trace amount of HCl to form the 3-hydroxyalkanenitrile.

2. The process of claim 1 wherein the alkenylnitrile is selected from the group consisting of 2-pentenenitrile, 3-pentenenitrile, 4-pentenenitrile and mixtures of these compounds, one with another or all three together.

3. The process of claim 1 wherein the process is continuous.

4. The process of claim 1 wherein the process is batch or semi-batch.

5. The process of claim 1 wherein the base is selected from the group consisting of alkali metal hydroxides, alkaline earth metal hydroxides, alkali metal carbonates, alkaline earth metal carbonates, tertiary amines; Lewis bases and strongly basic ion exchange resins.

6. The process of claim 5 wherein the base is in a form selected from the group consisting of a solution, an aqueous solution, solid particles or base supported on solid particles.

7. The process of claim 1 wherein following the formation of the 3-benzyloxyalkanenitrile adduct, the adduct is completely hydrogenated to form a 3-hydroxyaminoalkane.

* * * * *